United States Patent [19]
Bolton et al.

[11] Patent Number: 4,784,653
[45] Date of Patent: Nov. 15, 1988

[54] ABSORBENT ADHESIVE DRESSING

[75] Inventors: Laura L. Bolton, Metuchen; Teresa H. Haddock, Cranbury; Barry E. Constantine, Ocean Gate, all of N.J.

[73] Assignee: Johnson & Johnson Patient Care, Inc., New Brunswick, N.J.

[21] Appl. No.: 64,377

[22] Filed: Jun. 22, 1987

[51] Int. Cl.$^4$ ............................................. A61F 13/02
[52] U.S. Cl. ..................................... 604/307; 128/156; 428/284; 428/354; 428/355; 428/913; 428/192
[58] Field of Search ................................ 604/304, 307; 424/94.62; 128/155, 156; 428/261, 354, 913, 355, 284, 192

[56] References Cited

U.S. PATENT DOCUMENTS

| | | | |
|---|---|---|---|
| 3,725,122 | 4/1973 | Reinhard et al. | 428/355 |
| 3,728,148 | 4/1973 | Pietsch et al. | 428/261 |
| 3,740,366 | 6/1973 | Sanderson et al. | 428/354 |
| 4,655,768 | 4/1987 | Marecki et al. | 604/307 X |
| 4,657,006 | 4/1987 | Rawlings et al. | 604/307 X |
| 4,668,228 | 5/1987 | Bolton et al. | 424/94.62 X |
| 4,671,267 | 6/1987 | Stout | 604/304 X |
| 4,675,009 | 6/1987 | Hymes et al. | 604/307 X |

Primary Examiner—James J. Bell

[57] ABSTRACT

An absorbent adhesive dressing is disclosed which is intended for use in treating wounds of the ulcer and burn type where there is significant wound exudate, which has a three layer sandwich-type construction having an occlusive film (e.g. polyethylene, polypropylene etc.) as the outer layer, an absorbent layer of fibers (e.g. cellulose, synthetic fibers etc.) as the middle layer, and a wet-stick adhesive as the inner wound facing adhesive layer, wherein said adhesive layer is a continuous, substantially non-pourous layer having a porosity of less than 0.4 cc/sec/in$^2$ which is made from an acrylic polymer having both hydrophilic and hydrophobic characteristics (e.g. a wet-stick adhesive polymer formed from emulsion polymerization in water of N-vinyl caprolactam with n-butyl acrylate or with 2-ethylhexyl acrylate, or both, and which because of the hydrophilic nature of the polymer allows exudate to pass through the adhesive layer to the absorbent fibers of its middle layer without degrading the adhesive or its performance, and where the peripheral outer edges of the layers are optionally sealed.

16 Claims, No Drawings

ABSORBENT ADHESIVE DRESSING

This invention relates to absorbent adhesive dressings for use in treating wounds of the ulcer or burn type where there is significant wound exudate, and is more particularly concerned with such a dressing made in the form of a three layer sandwich type construction having an occlusive film as the outer layer, an absorbent layer of fibers as the middle layer, and a wet-stick adhesive as the inner, wound-facing layer, wherein the wet-stick adhesive layer is in the form of a continuous substantially non-porous layer made from an acrylic Polymer having both hydrophilic and hydrophobic characteristics and which allows wound exudate to pass through the adhesive membrane to the absorbent fibers of the middle layer without degrading the adhesive or its performance. The absorbent adhesive dressing may optionally contain a debriding enzyme on that part of the outer adhesive surface which contacts the wound. The dressings need not, but preferably will have their outer peripheral edges sealed.

BACKGROUND OF THE INVENTION

While many absorbent adhesive dressings are known, there is still room for improvement in moving closer to meeting the various desired properties of the ideal dressing for managing ulcer and burn wounds. Such wounds tend to exude much wound fluid exudate. What has been long sought, which the present invention offers, is a dressing which is especially absorbent, occlusive and adhesive, while providing an improved wound healing environment, and which manages exudate with the convenience of an adhesive facing so that no tape is needed to hold it in place.

Existing hydrocolloid absorbent adhesive dressings dissolve in the presence of wound fluid unless changed frequently, leaving a wound bed which must be cleaned before application of a fresh dressing. The particular adhesive used in the dressings of the present invention does not dissolve, but actually provides a relatively occlusive interface with the wound, while permitting exudate to pass gradually through it into the dressing's absorbent middle layer leaving the wound clean of both wound exudate and adhesive upon removal of the dressing from the wound. The adhesive serves the further function of being impervious to bacteria and other potential wound contaminants from exogeneous sources, i.e., those outside of the wound itself. Since the dressing is topped with an occlusive film outer layer e.g. polyethylene, it is impervious to bacteria and other potential wound contaminants. The preferred dressing manages wound fluid from a highly exudative wound for up to 3 days without exudate accumulation in the wound bed, while providing a moist environment which fosters repair.

Burns and ulcers are often debrided by use of a debriding enzyme applied thereto. Existing dressings which are occlusive enough to provide an optimal environment for repair permit puddling of exudate. When enzyme is applied under such existing dressings, the accumulated pools of exudate can wash away the debriding enzyme if the exudate escapes from under the dressing. In the embodiment of this invention wherein the debriding enzyme is applied to the face of the dressing, this is no longer a problem, because exudate does not Pool or escape from beneath the dressing. Because the adhesive layer uniquely slows exudate absorption, the enzyme on the adhesive face acts to dissolve necrotic tissue in the wound bed even though some exudate is constantly being absorbed by the dressing.

SUMMARY OF THE INVENTION

The present invention is directed to an absorbent adhesive dressing especially for use in treating wounds of the ulcer and burn type where there is significant wound exudate comprising: a three layer sandwich-type construction having an occlusive film as the outer layer, an absorbent layer of fibers as the middle layer, and a wet-stick adhesive as the inner wound facing adhesive layer, wherein said adhesive layer is a continuous, substantially non-porous layer having a porosity of less than 0.5 cc/sec/in2 which is made from an acrylic polymer having both hydrophilic and hydrophobic characteristics, and which because of the hydrophilic nature of the polymer allows exudate to pass through the adhesive layer to the absorbent fibers of its middle layer without degrading the adhesive or its performance. The absorbent adhesive dressing need not have, but preferably will have its outer Peripheral edges sealed A debriding enzyme may be added to the adhesive mass, if desired.

The dressings can be packaged and sterilized, so as to be available in sterile form at time of use.

Advantages of the Invention

The present invention provides the ulcer wound with (1) a self-adhesive dressing which (2) dissolves necrotic tissue thereby enhancing wound contraction rates and (3) optimizes repair, while (4) cleaning the wound of excess exudate. No existing dressing provides all four of the above functions at once.

The wet-stick adhesive used, makes the dressing convenient to apply, as well as playing an important role in maintaining an occlusive dressing interface with the wound, is hypo-allergenic and does not dissolve on the wound site like the hydrocolloid adhesives used in current ulcer dressings.

The dressing of this invention has the advantage of being self-adhesive, eliminating the need for tape to hold it in place. Unlike the prior art hydrocolloid dressings, the adhesive mass does not dissolve. Instead it leaves the wound bed clean and ready for the next dressing application, without need for manual wound cleaning. It works well as a debriding enzyme delivery system, and it can be sterilized by cobalt irradiation in this embodiment.

Moreover, this dressing construction allows some exudate absorption while maintaining a moist wound bed, which is sufficient to activate the debriding enzyme without washing it away from the wound bed.

DETAILED DESCRIPTION OF THE INVENTION

The present dressing has a sandwich-type construction with an occlusive film as the outer layer, an absorbent layer of fibers in the middle and an acrylic wet-stick adhesive on the side facing the wound. The adhesive dressing is protected by release paper which is to be removed at the time of use. The dressing is about 40-70 mils thick, preferably about 50 mils thick. The preferred construction utilizes a N-vinyl caprolactam-acrylic polymer wet-stick adhesive facing the wound, a unitized pad (FOSS) as the absorbent layer, and a polyethylene film as the outer layer, and has its outer peripheral edges sealed (to prevent airborne bacteria from entering through the sides of the dressing). Heat sealing is the easiest preferred way to seal the edges, but other ways are possible.

The Adhesive Layer

The adhesive used here is disclosed in pending U.S. patent application Ser. No. 674,390 of Haddock, filed Nov. 23, 1984 which is incorporated herein by reference. It is a wet stick adhesive which is satisfactory for application to human skin, especially to moist skin. The adhesive layer used in the dressings of the present invention is truly of a continuous layer, and is not microporous. It sticks to moist skin while allowing the wound exudate to pass through it because of its hydrophilic characteristics.

The wet-stick adhesive is formed by emulsion polymerization in water and is a polymer comprised of N-vinyl caprolactam with n-butyl acrylate or with 2-ethylhexyl acrylate, or with both of them, which gives superior skin wear adhesion in both dry and moist conditions. The preferred compositions for use in this invention are 95% n-butyl acrylate/5% N-vinyl caprolactam, 80% 2-ethylhexyl acrylate/20% N-vinyl caprolactam, 30% butyl acrylate/60% 2-ethylhexyl acrylate/10% N-vinyl caprolactam, and 79% 2-ethylhexyl acrylate, 15% N-vinyl caprolactam, 5% hydroxyethyl methacrylate and 1% acrylic acid.

The adhesives must exhibit viscoelastic behavior of a dynamic storage modulus of from 1.0 to $2.0 \times 10^5$ dynes/cm$^2$, a dynamic loss modulus of from about 0.5 to $1.0 \times 10^5$ dynes/cm$^2$, and a modulus ratio, tan $\delta$ = loss modulus/storage modulus, of from about 0.4 to 0.7 as determined at an oscillation frequency sweep of 1.0 rad/sec at 10% strain rate at body temperatures of 36° C.

Adhesives with moduli higher than the acceptable range have poor adhesion to skin especially at wet condition, while adhesives with moduli below the acceptable range exhibit poor cohesive strength and transfer large amounts of adhesive to the skin on removal. When the tan $\delta$ value is below 0.4, there will not be good skin adhesion. The above compositions must have the balanced viscoelastic properties as described in the range of moduli and tan $\delta$.

Other functional polar monomers can be used in conjunction with N-vinyl caprolactam with either n-butyl acrylate or 2-ethylhexyl acrylate or with both of them at a level lower than the concentration of N-vinyl caprolactam. The desirable compositions are 80% 2-ethylhexyl acrylate/15% N-vinyl caprolactam/5% 2-hydroxyethyl methacrylate and 80% 2-ethylhexyl acrylate/18% N-vinyl caprolactam/2% acrylic acid. 2-hydroxyethyl methacrylate or acrylic acid may be used in the adhesive composition providing the moduli and tan 6 are maintained at the desirable value.

The most preferred wet-stick adhesive for use in the ulcer dressing of the present invention has a composition of 78.5% 2-ethylhexyl acrylate/15% N-vinyl caprolactam/5% hydroxyethyl methacrylate/1.5% acrylic acid [78.5% 2 EHA/15% NVCL 5%HEMA/1.5% AA]. The adhesive layer can range from 2 to 10 mils thick. The preferred thickness is 3 to 5 mils. In the most preferred adhesive the 2-ethylhexyl acrylate part of the polymer is hydrophobic while the balance of the polymer is hydrophilic.

The Absorbent Fiber Layer

The absorbent middle layer of fibers can be of any conventional absorbent woven or nonwoven materials or synthetic foam. Cellulosic materials such as wood pulp, cotton etc., or synthetic fibers such as polyester, polypropylene, etc. are typical non-limiting examples. The absorbent fiber layer is commercially available either as a separate pad or with an occlusive film layer backing i.e. as a unitized pad. We currently prefer a unitized pad of a thick cushion-type occlusive construction, which is made of 90 percent polypropylene/10 percent rayon fibers, laminated to polyethylene on one side [available from FOSS]. The middle fiber layer not only absorbs the excess exudate which penetrates the adhesive, but also provides a cushion which can prevent pressure to delicate wounds. The thickness of the absorbent layer of fibers can be varied from 10 to 90 mils. The preferred range is 40 to 60 mils. The absorbent layer should have the capacity to absorb about 0.5 ml of wound fluid per square cm of wound area per day.

The absorbent layer should have the capacity to absorb the amount of wound exudate expected to be exuded. This varies depending on the type of wound from a minimal amount up to as much as about 1.5 ml of fluid per square cm of wound area per day. The water absorption rate of a 50 mil thick dressing can range from 10 to 40 mg/cm$^2$/minute Total water absorption capacity of the dressing is in the range of 800 to 2000 mg/cm$^3$.

The Occlusive Film Layer

The outer polyethylene layer, which must be a continuous layer without any holes, serves as an occlusive film layer. In that embodiment of the invention where the edges of the dressing are all sealed, the outer layer provides a barrier to bacteria and external contaminants while providing occlusive properties to the dressing.

Other polymeric films such as polypropylene, polyurethane, polyester and vinyl also can be used as an occlusive outer layer. The specific thickness is relatively unimportant, but likely will vary from about 0.2 to 1.5 mils.

The Debriding Enzymes

The dressing of the present invention, in its debriding enzyme-containing embodiment, has the same basic construction as the ulcer dressing described above, except that a debriding enzyme is added so it covers part of the adhesive side of the dressing, and is protected by being covered with release paper. The preferred enzyme dressing has a thickness of 40 to 60 mils, which is the same as for the non-enzyme dressing. The adhesive thickness of the enzyme dressing preferably should be at least 3 mils, while the most preferred thickness range is 4 to 7 mils thick. In other words, the enzyme containing embodiment usually has a slightly thicker adhesive layer than when enzyme is not used.

The preferred enzyme-containing dressing construction utilizes a 90% polypropylene/10% rayon absorbent layer of 50 mils thickness which has been fused with 1 mil thick polyethylene as backing, with the previously described wet-stick adhesive, being partially covered with the debriding enzyme, subtilisin or, with any other debriding enzyme so the enzyme will be facing the wound.

The debriding enzymes useful in the dressings of the present invention are proteolytic enzymes known to be useful for debridement of eschar and necrotic tissue to permit wound healing and include papain, trypsin, collagenase, subtilisins A and B, ficin, pepsin, lysozyme, streptokinase, fibrnolysin, pinguinain, bromelain "escharase" fraction of bromelain, chymotrypsin, pancreatic lipase, n-acetylcysteine, and enzyme products derived from bromelein. For reasons of availability, ease of obtaining regulatory approval, and economy, we prefer to use Subtilisin A or B as our most preferred debriding enzyme, with other preferred debriding enzymes being active fractions of bromelain or other pharmaceutically acceptable enzymes.

The debriding enzymes which are useful in the present invention are solids capable of being ground into powder form. This allows them to be easily distributed relatively evenly. The debriding enzyme is most desirably applied to the surface of the adhesive mass to be placed nearest the necrotic tissue because it has been found most efficacious to apply the full quantity of enzyme directly to the eschar which is to be debrided. If enzyme is incorporated in the adhesive mass, this will also work but not as well; or at least the portion of the enzyme which is incorporated within the adhesive mass would take longer to have any effect on the eschar because of its slower delivery. Thus, the most desired version of the debriding dressing of the present invention would have substantially all of the debriding enzyme applied to the outer surface where it is immediately available.

The quantities of enzyme on the debriding dressing are not critical, but it is desired that a relatively large amount be applied to the critical areas at once. We have found that amounts on the order of from 0.5 mg of subtilisin A or (885 PCU[1]) to 5 mg or 8850 PCU/cm$^2$ of burn area can be used, depending on the depths of necrotic tissue to be removed. What is desired is to use an effective debriding amount of the particular enzyme used.

[1]PCU is an abbreviation of Proteolytic Casein Units as defined in the Food Chemicals Codex, 3rd Edition, pages 495-496. One PCU is that quantity of enzyme that produces the equivalent of 1.5 $\mu$g/ml of L-tyrosine per minute of incubation with a standard casein solution at 37° C., PH 7.0.

The effective amount could differ depending upon the desired application. For example, for burns the amount would be generally on the order of 885 PCU/cm$^2$ while for deeper ischemic ulcers, the amount would be generally on the order of 2000-3000 PCU/cm$^2$. It is possible to equate many of the various proteolytic enzymes which may be used by referring to units of casein hydrolysis activity (PCU), so if the same units are used, then the different amounts necessary of the specific debriding enzyme which is chosen can be equated. On the other hand, some enzymes, such as the escharase fraction of bromelain, may require definition of their activity in other types of units.

The wet-stick adhesive provides several advantages in this enzyme dressing. It retards evaporation of wound fluids sufficiently to maintain a physiologically moist wound bed, optimizing repair, and it adheres to the skin in the presence of moisture. The preferred wet-stick adhesive for use with enzyme is a polymer of 78.5 percent 2-ethylhexyl acrylate/15 percent N-vinyl caprolactam/5 percent hydroxyethyl methacrylate/1.5 percent acrylic acid. While this adhesive layer can be 2-10 mils thick, it is preferably at least 3 and most preferably 4-7 mils thick for maximum efficiency.

Debriding enzymes Placed on the adhesive face of the present absorbent dressing works nearly as well as those Placed on occlusive, adhesive nonabsorbent films described in U.S. patent application Ser. No. 710,817 filed Mar. 12, 1983 entitled "Debriding Tape". The main advantage over that construction is that exudate does not accumulate in such large amounts under the present construction. This prevents the enzyme from being washed away in case exudate seeps from beneath the dressing.

General Method of Preparing the Dressing

The absorbent layer of fibers and the occlusive film layer are laminated together using heat and pressure, forming a unitized pad, then the desired wet-stick adhesive is coated on release paper by using a standard reverse-roll coater. After drying the adhesive (to remove at least 99% of water) through a series of oven temperature ranges from 150° to 350° F., the continuous adhesive film is laminated under heat (0.150° F.) and pressure (300–400 psi) to the unitized pad. Later, the dried laminate is slit and heat die-cut into the desirable dressing size. Typical sizes include 4×4 in$^2$, 2×2 in$^2$ or 6×6 in$^2$. The finished dressing, whose peripheral edges all have been heat sealed, is packaged in a pouch which then is sealed and sterilized e.g. by Cobalt irradiation. Where enzyme is to be applied, this can be placed on the dried adhesive surface of the finished dressing e.g. by removing the release paper, applying enzyme and then reapplying release paper. Where the dressing contains enzyme, it should be packaged only in a waterproof container.

The dressings were evaluated by the following procedure; and results reported in Table I.

Experimental Model and Results

The Model

The guinea pig ischemic ulcer model is a modification of one described in detail in B. E. Constantine et al. article entitled "A Wound Model for Ischemic Ulcers in the Guinea Pig" Arch Dermatol Res (1986) 278:429–431. A hard rubber flanged cylinder is placed beneath the dorsal flank skin of an anesthetized guinea pig. The skin and underlying cylinder are encircled tightly by a rubber band, which acts as a tourniquet, cutting off the blood supply to the skin immediately over the cylinder for 24 hours. The rubber band and cylinder are then removed, and the ischemic skin becomes necrotic.

Before the study began, six guinea pigs per treatment condition were dipilated using Zip Wax. After four days all subjects received mid-dorsal subcutaneous implants with an extracutaneous tourniquet which maintained ishemia in a six cm$^2$ circle of dorsal skin. The tourniquet was released 24 hours later and the implant removed, leaving a full-thickness necrotic defect. To generate the hard blackened eschar normally associated with decubiti, the wounds were permitted to mature, air-exposed, for six days before treatment began.

Prior to dressing application, all wound areas were photographed, traced and area determinations made using an OPTOMAX System III Image Analyzer.

Dressings were applied to the six-day-old necrotic ulcer and held in place with adhesive tape for three days. After necrotic tissue separation, dissolution and wound bed cleaning were noted, the wounds were photographed, and wound areas were traced for later area determination. Fresh dressings were then applied, which remained in place for four more days. After a total of seven days of treatment, all subjects were sacrificed, and the observations, photographs and area measurements were repeated.

Percent wound contraction was determined at day three and day seven as [(Day 0 Area−Day 3 or Day 7 Area)/Day 0 Area]*100. Higher contraction rates indicate more rapid healings.

Necrotic tissue separation was defined as the necrotic tissue lifting from at least half of the wound bed. Dissolution of the necrotic tissue meant that it could be removed from the wound bed by irrigation or by wiping with a sponge. Wound cleaning occurred when the surrounding intact skin and repairing granulation tissue beneath the dressing were clearly visible upon dressing removal.

Contraction data were analyzed using analysis of variance with the Newman-Keuls test to compare individual means. A confidence interval of 95 percent or above was considered statistically significant.

The following are examples of the dressings of the present invention, or are control examples of prior art dressings used for purposes of comparison.

EXAMPLE 1

The ulcer dressing of Example 1, which is a non-enzyme-containing dressing of the present invention, was made by the General Method previously described, and cut to a 2"×2" size. The dressing was protected by release paper before application. The specific adhesive used was the preferred wet-stick adhesive having a composition of 78.5% 2EHA/15% NVCL/5%HEMA/1.5% AA applied at 3.8 mils thickness. The absorbent middle layer of fibers (50 mil thick) made of 90% polypropylene/10% rayon was laminated to an outer 1 mil thick polyethylene film layer. The ulcer dressing of this Example 1 was used on guinea pig ulcer model. After the first three days treatment, all ulcer wounds showed significantly higher wound contraction rates (of average 0.18%) than controls, e.g. when compared with other treatment groups in the study (Table I) and than the commercial product Duoderm (Squibb, Example 2). The wound bed was very clean. After the second four days applications on the same ulcer wounds, they showed 0.58% contraction and only very slight accumulation of exudate and dissolved necrotic tissue. Most of the exudate was absorbed in the middle absorbent layer. The wet-stick adhesive part of the dressing retained its physical form of a continuous adhesive film. The results are summarized in Table I.

CONTROL EXAMPLE 2

Using the same animal model, a commercial ulcer dressing Duoderm (Squibb) was used as a control experiment to Example 1. After the first three days of treatment, the ulcer wounds showed 6% contraction. The dressing adhesive dissolved on all ulcers, leaving an accumulation of caramel-like, high viscosity hydrocolloid mass on the wound surface and margin. Underneath there are a slight to moderate amount of accumulation of exudate and dissolved necrotic tissue on the wound bed. After a second application for four more days (Day 7), the same hydrocolloid adhesive mass disintegration had occurred on all ulcers, and a great amount of accumulation of exudate and dissolved necrotic tissue were present in the wound bed. A significantly lower wound contraction of 35% as compared to the present invention (Example 1)

CONTROL EXAMPLE 3

A commercial film dressing, BIOCLUSIVE6 (Johnson & Johnson Products) was used as another control to Example 1 on the animal model. (Since it does not have the absorbable fiber middle layer or the wet-stick adhesive to exchange the dressing skin adhesion.) The wounds did not display much exudate accumulation after the first three days or the second four days as the exudate leaked away from the wound bed through small wrinkles in the dressing. Although it showed a remarkable 18% wound contraction after day three and 48% wound contraction after day seven, it lacks the ability to manage the exudate as Example 1 does.

CONTROL EXAMPLE 4

The dressing of Example 4 is an enzyme-containing dressing of the present invention. It was made by using the same ulcer dressing as in Example 1 to which 2 mg of Subtilisin A (Novo Labs, Inc.) containing a total of 400 Proteolytic Casein Units of enzyme activity, were placed on that part of the outer surface of the adhesive mass intended to cover the guinea pig wound. This ulcer dressing with enzyme debriding agent had showed excellent wound contraction of 27% and 67% for day three and day seven respectively. (See Table I.) After three days of application, the wound bed was as clean as with the dressing of Example 1. After the second four days application, the wound bed had slight accumulation of exudate and dissolved necrotic tissue. However, the dressing debrided all the ulcer necrotic tissue.

CONTROL EXAMPLE 5

This Control Example used the same dressing as Example 2 (Duoderm, Squibb), to which 2 mg of Subtilisin A (Novo Labs, Inc.) were placed on the adhesive mass (as in Example 4). The wound contraction and wound bed cleanliness results were similar to those of Example 2. Just as with Example 2, the hydrocolloid adhesive disintegrated and adhered to the wound bed. The enzyme on this Example 5 dressing softened, but did not dissolve the necrotic tissue as the dressing in Example 4 did.

TABLE I

| Evaluation of Ulcer Dressing | Day 3 | | Day 7 | |
| --- | --- | --- | --- | --- |
| | Wound Contraction | Wound Bed Cleaning | Wound Contraction | Wound Bed Cleaning |
| Example 1 Unitized pad | 18% | 0 | 58% | 1.0 |
| Control Example 2 Duoderm | 8% | 1.5 | 35% | 3.0 |
| Control Example 3 Bioclusive Film | 18% | 1.0 | 48% | 1.5 |
| Control Example 4 Unitized pad plus 2 mg of Subtilisin A | 27% | 0 | 67% | 1.0 |
| Control Example 5 Duoderm plus 2 mg. of Subtilisin A | .1% | 1.5 | 30% | 3.0 |

Cleanliness Scale Used:
0 - Very clean
1 - Slight accumulation of exudate and dissolved necrotic tissue
2 - Moderate accumulation of exudate and dissolved necrotic tissue
3 - Great accumulation of exudate and dissolved necrotic tissue Examples 1, 4 and 3 demonstrated more rapid contraction rates after 3 days. Examples 1 and 4 removed debris from the wound site, while the remaining Control Examples did not.

The Examples of the present invention, Examples 1 and 4, are clearly superior.

We claim:

1. An absorbent adhesive dressing especially for use in treating wounds of the ulcer and burn type where there is significant wound exudate comprising: a three layer sandwich-type construction having an occlusive film as the outer layer, an absorbent layer of fibers as the middle layer, and a wet-stick adhesive as the inner wound facing adhesive layer, wherein said adhesive layer is a continuous, substantially non-porous layer having a porosity of less than 0.5 cc/sec/in$^2$ which is made from an acrylic polymer having both hydrophillic and hydrophobic characteristics and said adhesive layer comprising a mixture of: (a) N-vinyl caprolactam and (b) n-butyl acrylate or 2-ethylhexyl acrylate or a combination thereof.

2. The dressing of claim 1 wherein the peripheral outer edges of the layers are all sealed.

3. The dressing of claim 1 wherein the adhesive layer is a wet-stick adhesive polymer formed from emulsion polymerization in water, comprising N-vinyl caprolactam with n-butyl acrylate or with 2-ethylhexyl acrylate, or both in the polymer 4. The dressing of claim 2 wherein the adhesive layer is from 2 to 10 mils thick.

5. The dressing of claim 4 wherein the adhesive layer is 3-7 mils thick

6. The dressing of claim 1 wherein the absorbent middle layer is a pad having a thickness of 10 to 90 mils, and capable of absorbing 800-2000 mg/cm$^3$ of water 7. The dressing of claim 6 wherein the pad is a thick cushion-type construction made of 90% polypropylene and 10% rayon fibers 8. The dressing of claim 7 wherein the pad has a thickness of 40-60 mils 9. The dressing of claim 1 wherein the occlusive film outer layer is made of polyethylene, polypropylene, polyurethane, polyester or vinyl polymeric films 10. The dressing of claim 9 wherein the occlusive film outer layer has a thickness from about 0.2-1.5 mils 11. The dressing of claim 10 wherein the occlusive film outer layer is polyethylene, which is laminated to the middle layer 12. The dressing of claim 1 having a debriding enzyme in or on the adhesive layer 13. The dressing of claim 2 having a debriding enzyme on the inner wound facing surface of the adhesive dressing 14. The dressing of claim 13 wherein the debriding enzyme used is Subtilisin A or B.

15. The dressing of claim 1 packaged in sterile form.

16. The dressing of claim 13 packaged in sterile form.

* * * * *

UNITED STATES PATENT AND TRADEMARK OFFICE
CERTIFICATE OF CORRECTION

PATENT NO. : 4,784,653
DATED : November 15, 1988
INVENTOR(S) : Laura L. Bolton; Teresa H. Haddock; Barry E. Constantine It is certified that error appears in the above-identified patent and that said Letters Patent is hereby corrected as shown below:

In the Abstract:

Line 11 change "0.4" to -- 0.5--.

Signed and Sealed this

Twenty-third Day of May, 1989

Attest:

DONALD J. QUIGG

*Attesting Officer*  *Commissioner of Patents and Trademarks*